(12) United States Patent
Shaw et al.

(10) Patent No.: US 6,872,193 B2
(45) Date of Patent: Mar. 29, 2005

(54) IV CATHETER INTRODUCER WITH RETRACTABLE NEEDLE

(75) Inventors: Thomas J. Shaw, Little Elm, TX (US); Judy Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 377 days.

(21) Appl. No.: 10/047,662

(22) Filed: Oct. 26, 2001

(65) Prior Publication Data

US 2003/0083621 A1 May 1, 2003

(51) Int. Cl.[7] ............................................... A61M 5/00
(52) U.S. Cl. ................... 604/164.07; 604/110
(58) Field of Search .................. 604/500, 506–508, 604/110, 161, 164.01, 164.02, 164.04, 164.06, 164.07, 164.11, 164.12, 167.01, 167.02, 195, 198; 600/573

(56) References Cited

U.S. PATENT DOCUMENTS

| | | | |
|---|---|---|---|
| 5,746,215 A | 5/1998 | Manjarrez | 128/763 |
| 5,817,058 A | 10/1998 | Shaw | 604/110 |
| 5,989,220 A | 11/1999 | Shaw et al. | 604/110 |
| 6,083,202 A | 7/2000 | Smith | 604/164 |
| 6,090,078 A | 7/2000 | Erskine | 604/198 |
| 6,096,005 A * | 8/2000 | Botich et al. | 604/110 |

\* cited by examiner

Primary Examiner—Kevin C. Sirmons
(74) Attorney, Agent, or Firm—Locke Liddell & Sapp LLP; Kristen R. Paris

(57) ABSTRACT

An IV catheter introducer having a retractable needle holder and a tubular plunger that are held by a detent structure in a preferred positional relationship prior to and during insertion of the catheter. Following insertion, the plunger is pushed past the detent structure, permitting a compressed spring to force the needle holder upwardly into the plunger. A vented end cap in the plunger permits rapid venting of air displaced during retraction of the needle holder. The needle holder includes a flash chamber that is easily viewable through a clear plastic housing. Wings are provided on the housing to facililate one-handed operation of the device. A method for assembling the subject catheter introducer is also disclosed.

66 Claims, 3 Drawing Sheets

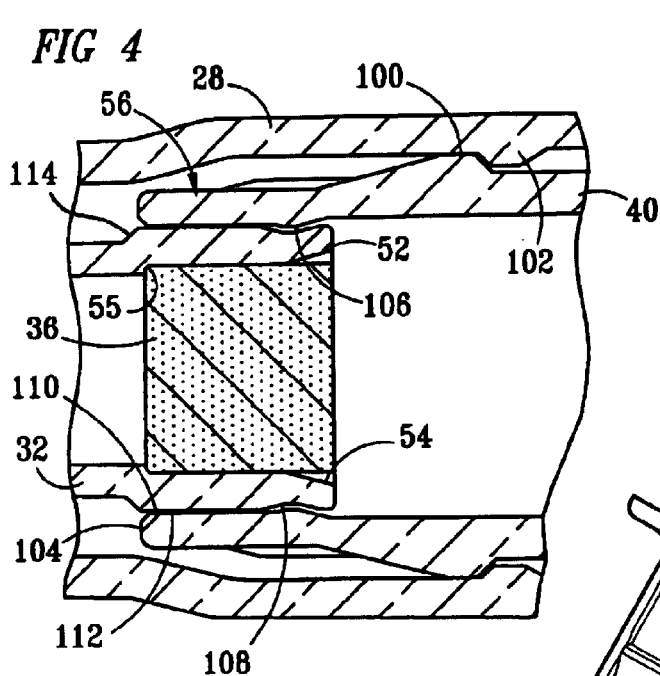
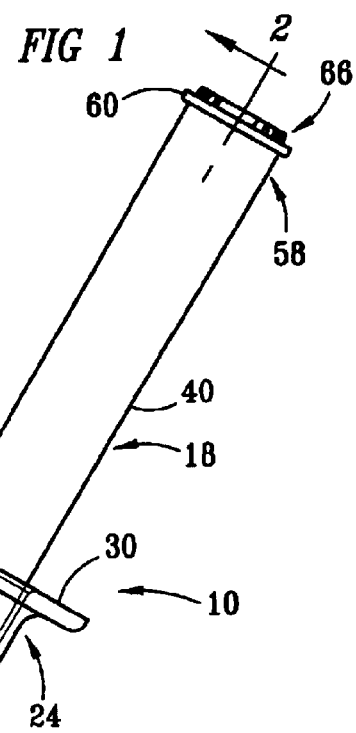
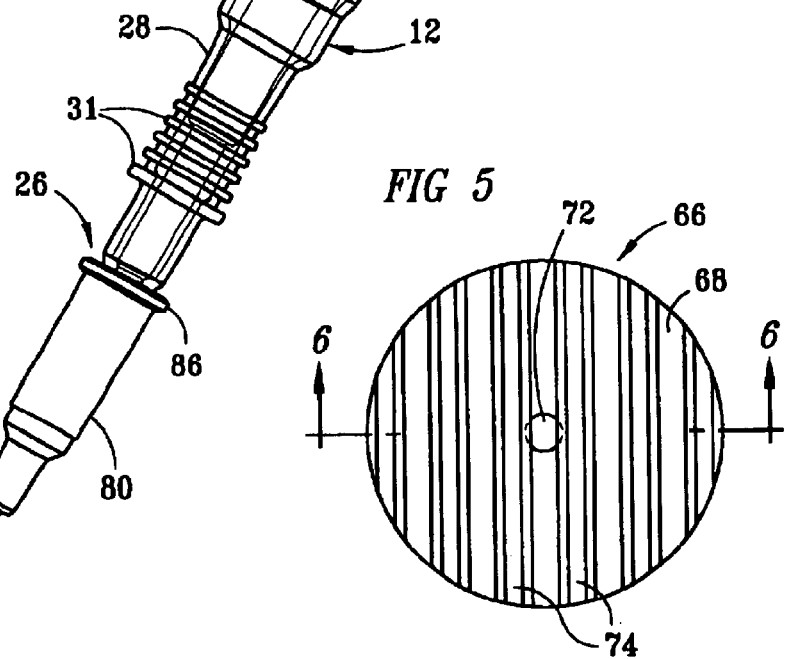
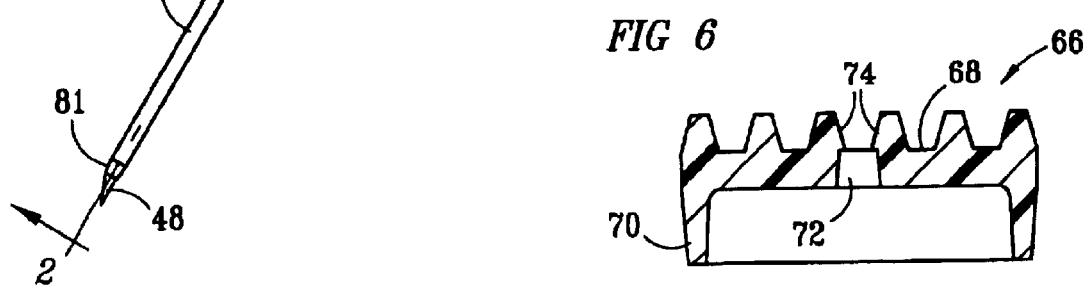

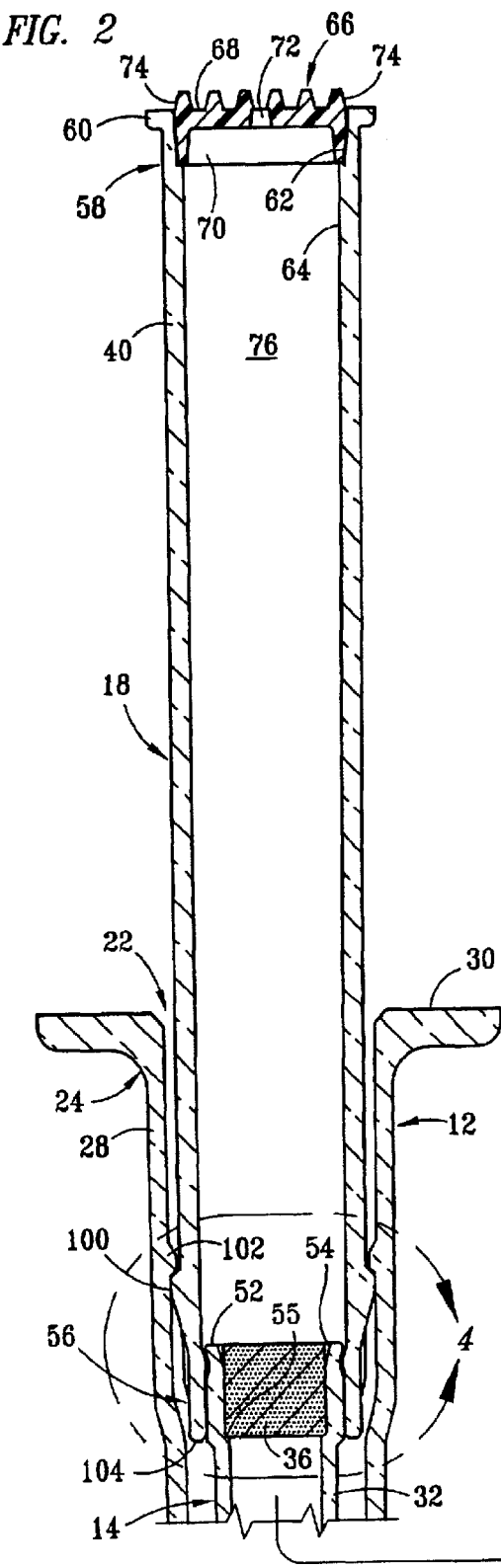
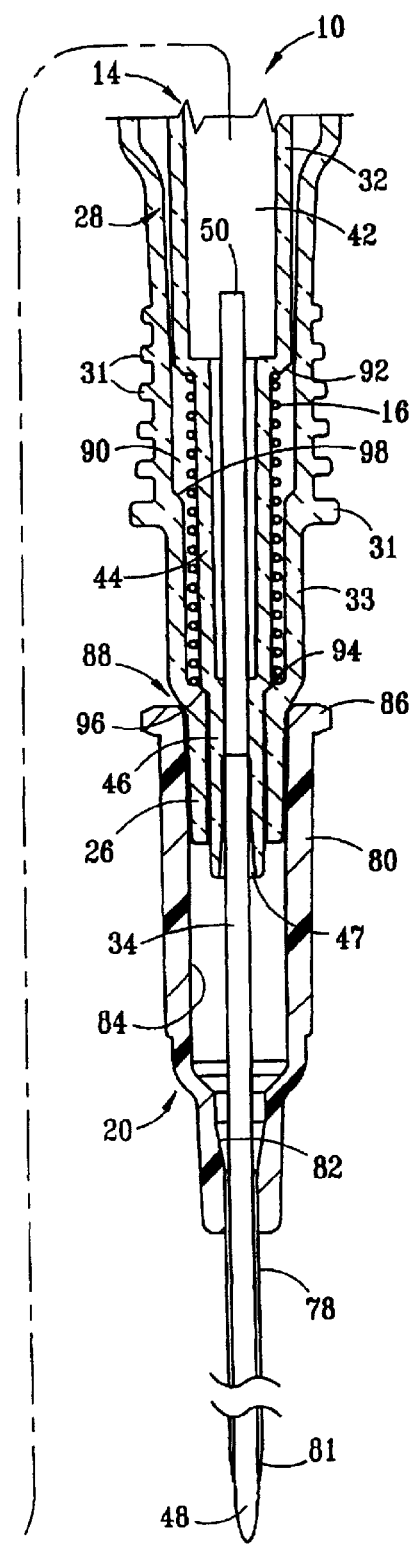
FIG. 2

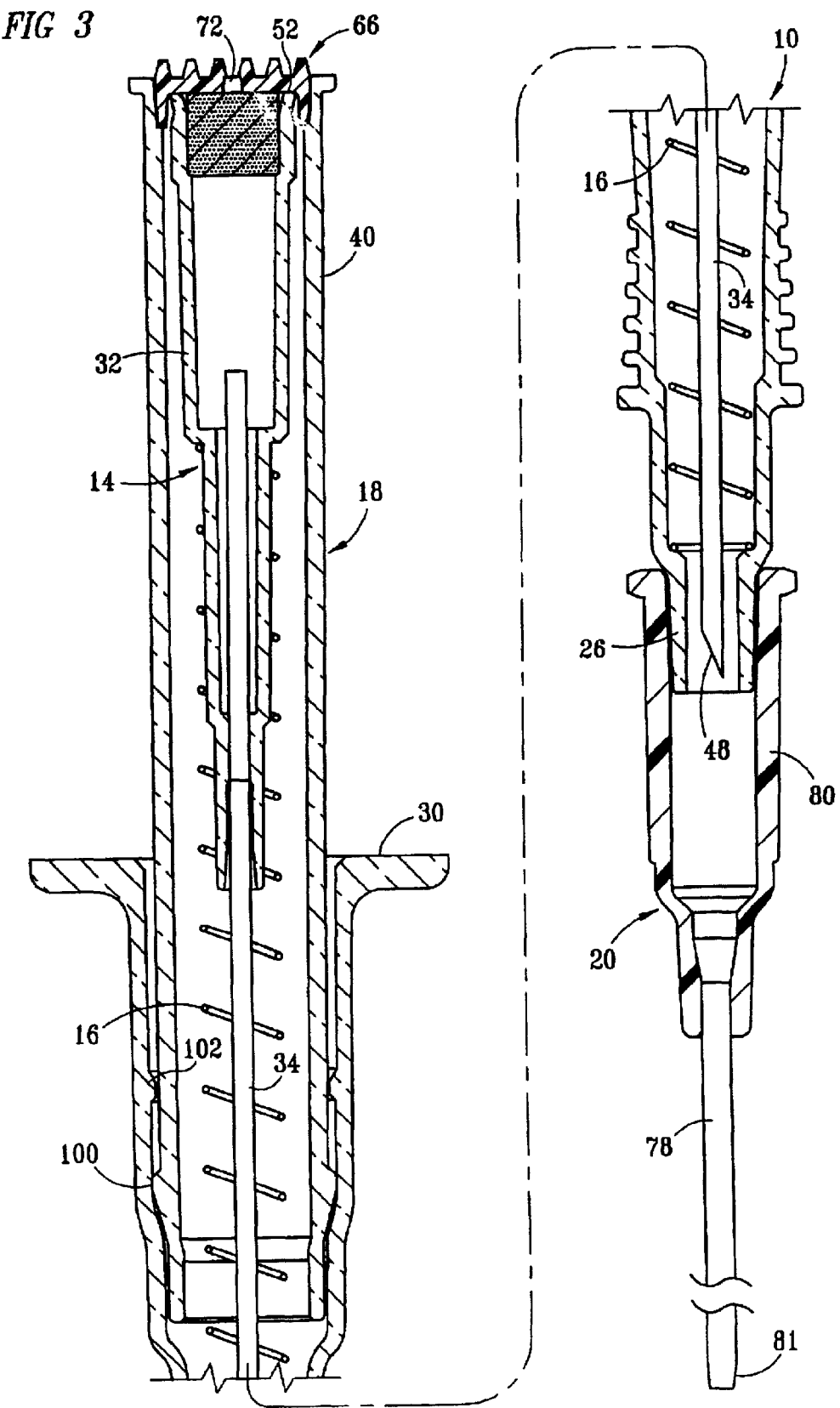

IV CATHETER INTRODUCER WITH RETRACTABLE NEEDLE

BACKGROUND OF THE INVENTION

1. Field of the Invention

The invention is a medical device used to insert a catheter into a patient's body, especially for the intravenous delivery of a fluid. More particularly, the invention is a catheter introducer having a retractable needle that prevents reuse and avoids needle stick injuries to medical personnel and others.

2. Description of Related Art

Catheter insertion devices are well known. When a catheter is inserted into a patient for the intravenous delivery of a fluid, a disposable needle passing through the catheter is utilized to puncture a vein to permit entry of the catheter. The needle is then withdrawn, leaving the catheter in place for connection to an IV bag or bottle, or to be capped for later use.

In recent years, because of the prevalence of blood-borne pathogens such as HIV and hepatitis, there has been an increasing need for catheter introducers that prevent accidental needle stick injuries to medical personnel and to other employees who handle trash, laundry or other refuse containing used needles. As a result, new products have been designed that incorporate special needle covers or mechanisms for retracting the needle following use. Such devices are disclosed, for example, in U.S. Pat. Nos. 4,747,831; 4,828,548; 5,129,884; 5,501,675; 5,817,058 and 5,989,220. Many of the prior art devices contain numerous complicated parts that substantially increase manufacturing costs and interfere with the user's ability to feel when the needle is properly inserted into the patient. Other devices require two-handed operation or are prone to premature needle retraction during shipment, storage and handling.

An IV catheter introducer is therefore needed that can be manufactured economically and reliably at high speed, that will not retract the needle prematurely, that can be operated with one hand, and that will fully protect the user and others from accidental sticks and exposure to blood-borne pathogens. These and other advantages are provided by the invention disclosed below.

SUMMARY OF THE INVENTION

A single use IV catheter introducer is disclosed that provides significant advantages over prior art devices, even those comprising retractable needles. Principal structural improvements include a reliable detent structure that holds the needle holder and plunger in proper positional alignment prior to needle retraction; following insertion of the catheter; a plunger end cap that vents air displaced from inside the plunger bore during needle retraction; and a transparent viewing area that permits the user to view the flash chamber of the needle holder more easily through the clear plastic housing. Other improvements include barrel wings that facilitate one-handed operation and prevent the catheter introducer from rolling when placed on a surface, a needle holder opening that is tapered to permit easy insertion of the flash chamber plug during manufacture, and a needle holder configuration that prevents the blunt needle end from being occluded during manufacture and makes the flow of blood into the flash chamber more visible.

The IV catheter introducers of the invention have few parts, can be manufactured reliably at high speed, significantly reduce the likelihood of premature needle retraction during storage and handling, are easily useable in one hand, and will protect medical and other ancillary personnel from accidental needle sticks and the possibility of resultant infection by blood-borne pathogens. Use of the present invention also affords significant economic benefits to health care providers and insurers through reduced testing and follow-up costs.

BRIEF DESCRIPTION OF THE DRAWINGS

The apparatus of the invention is further described and explained in relation to the following figures of the drawing wherein:

FIG. 1 is a simplified perspective view of the IV catheter introducer of the invention with the catheter needle ready for use;

FIG. 2 is an enlarged, cross-sectional elevation view taken along line 2—2 of FIG. 1;

FIG. 3 is a view as in FIG. 2, but with the needle retracted following use;

FIG. 4 is an enlarged detail view taken from FIG. 2, and depicts the detent structure holding the landed front opening of the plunger tube in the desired position relative to the retractable needle holder prior to retraction;

FIG. 5 is an enlarged plan view of the vented plunger end cap; and

FIG. 6 is a cross-sectional elevation view taken along line 6—6 of FIG. 5.

Like reference numerals are used to describe like parts in all figures of the drawings.

DETAILED DESCRIPTION OF THE PREFERRED EMBODIMENT

Referring to FIGS. 1–2, IV catheter introducer 10 preferably comprises tubular plastic housing 12, needle holder assembly 14, retraction mechanism 16, plunger assembly 18 and IV catheter 20. Plastic housing 12 has an internal bore 22 that narrows progressively between open end 24 and reduced diameter tip 26, except for a short distance below inwardly projecting annular ring 102, as described below. Plastic housing 12 is preferably injection molded from a substantially transparent polymeric resin such as polycarbonate to permit easy viewing through sidewall 28. The outside diameter of housing 12 generally follows the tapered narrowing of internal bore 22, so that sidewall 28 has a substantially constant thickness except where it flares outwardly to form laterally extending wings 30 and to provide a longitudinally spaced series of annular ridges 31 nearer to tip 26 to create a textured gripping area for the fingers of the user.

Needle holder assembly 14 is retractably mounted within the lower portion of housing 12 and preferably comprises a tapered, elongate tubular body 32, needle 34 and porous plug 36. Body 32 of needle holder assembly 14 is preferably injection molded from a substantially transparent polymeric resin such as polycarbonate and comprises a tapering sidewall of substantially constant thickness that further defines flash chamber 42, spring guide section 44 and needle support section 46, each of which has a progressively smaller diameter. Tubular body 32 of needle holder assembly 14 is desirably shaped so as to permit needle holder assembly 14 to be inserted into sliding engagement with housing 12 during assembly, as described in greater detail below. The upper end portion of tubular body 32 is adapted to releasably engage lower end 56 of plunger assembly 18 as described below in relation to FIG. 4. As viewed in FIG. 2, retraction mechanism 16, which is preferably a spring, is confined within annular space 90 between housing 12 and spring guide section 44 of tubular body 32, and is held in compression between downwardly facing shoulder 92 of tubular body 32 and upwardly facing shoulder 94 of housing 12. Although this embodiment uses a compressed spring that exerts a retraction force by expanding, other similarly effective means such as an extension spring can likewise be used to retract the needle.

Needle 34 is hollow and has a beveled end 48, which is inserted into a patient's vein during use, and a blunt end 50 that extends into flash chamber 42. A longitudinally extending bore provides fluid communication through needle 34 between beveled end 48 and blunt end 50. Needle 34 is preferably insert molded into needle support section 46 of tubular body 32 to create an insert molded needle. However needle 34 can be glued or sonically welded into body 32 if desired. A tapered needle insertion opening 47 is desirably provided at the lower end of needle support section 46 if needle 34 is to be inserted after molding needle support section 46. By using a needle 34 that is long enough to extend into flash chamber 42, the bore of needle 34 will not become occluded during insert molding. Also, because a minor amount of blood flows upwardly through needle 34 into flash chamber 42 whenever needle 34 is introduced into the vein of a patient, making blunt end 50 visible in flash chamber 42 permits the user to view blood as soon as it enters flash chamber 42, confirming to the user that needle 34 is properly positioned inside the vein.

At the top of flash chamber 42 of needle holder assembly 14, end 52 of tubular body 32 is blocked with porous plug 36 that frictionally engages the walls of annular recess 55 in body 32. The insertion of porous plug 36 into tubular body 32 is preferably made easier by tapered inside wall 54 adjacent to end 52. Porous plug 36 is preferably made of any suitable porous material that will allow air to be displaced out of needle 34 and flash chamber 42 by blood rising through needle 34 following insertion into a vein, but will prevent any such minor amount of blood from exiting flash chamber 42. A significant advantage of IV catheter introducer 10 disclosed herein is that flash chamber 42 is visible through only two layers of clear plastic: the transparent wall of tubular body 32 around flash chamber 42; and the transparent wall of housing 12. With many devices disclosed in the prior art, the user must peer through three or more plastic layers to view the flash chamber, making it more difficult to observe when blood begins entering the chamber.

Plunger assembly 18 preferably comprises a polymeric plunger tube 40 having a substantially cylindrical sidewall with a lower end portion 56 that is proximal to end 52 of tubular body 32 of needle holder assembly 14, and an upper end portion 58 that projects longitudinally outward from open end 24 of housing 12. Plunger tube 40 is preferably injection molded from a polymeric resin, and most preferably, from a substantially transparent polymer such as polycarbonate. Lower end portion 56 of plunger assembly 18 releasably engages tubular body 32 of needle holder assembly 14 and cooperates with needle holder assembly 14 to form the detent structure of the invention as described in greater detail below in relation to FIG. 4. Upper end portion 58 of plunger tube 40 preferably comprises a small, radially extending annular flange 60 surrounding a tapered annular recess 62 in surface 64 that receives and frictionally engages end cap 66, which is further described and explained in relation to FIGS. 5 and 6. With IV catheter introducer 10 prepared for use, upper end 58 of plunger assembly 18 desirably extends from about 1.5 to about 3 inches from housing 12 so that upper end 58 can be nestled against the palm of the hand while the user's fingers grip wings 30 or annular ridges 31 of housing 12 to facilitate one-handed operation. Pulling back on housing 12 with the fingers triggers retraction of needle holder assembly 14, as discussed below in relation to FIG. 3.

Referring to FIGS. 5 and 6, end cap 66 is preferably molded from a polymeric resin and, most preferably, from a resin that is pigmented in a color chosen to correspond to the gauge of needle 34, shown in FIGS. 1–2, to assist users in readily differentiating among IV catheter introducers 10 having different sized needles. End cap 66 preferably further comprises a substantially continuous, circular end wall 68 connected to a longitudinally extending annular skirt 70 that is inwardly tapered to provide contacting frictional engagement with annular recess 62 of plunger tube 40 as previously described. It should be understood that there are many ways of engaging end cap 66 into upper end portion 58 of plunger tube 40. End cap 66 may be glued, snapped-on, sonically welded, dual shot molded or engaged by any other similarly effective means. Dual shot molding refers to any molding process that allows different materials or different colored materials to be molded concurrently. Vent hole 72 is preferably centrally disposed in end wall 68 and is desirably surrounded by surface relief features such as a plurality of outwardly extending molded ribs 74 that extend across surface 68. Ribs 74 are preferably of sufficient number, spacing and height that vent hole 72 is not blocked by the hand of the user, even when part of the hand is placed over end cap 66 during operation of IV catheter introducer 10. Vent hole 72 is preferably large enough to rapidly vent the volume of air displaced from retraction cavity 76 when needle holder assembly 14 is retracted into plunger tube 40 following insertion of the catheter.

Referring again to FIGS. 1–2, IV catheter 20 preferably includes a flexible rubber or plastic cannula 78 and a hub 80 having a needle channel 82 and a tubular section 84 with an annular flange 86 defining an opening 88 having a diameter such that opening 88 will receive and frictionally engage tip 26 of housing 12. At the end of cannula 78 is an inwardly tapered end 81 that provides an interference fit near beveled end 48 of needle 34. During the attachment of hub 80 to tip 26, needle 34 is inserted through flexible cannula 78 and inwardly tapered end 81, with beveled end 48 extending slightly beyond the inwardly tapered end 81. The inside diameter of cannula 78 is preferably slightly greater than the outside diameter of needle 34 to permit easy retraction of needle 34 through cannula 78 following insertion. Hub 80 is preferably also adapted for easy connection to a convention IV tubing connector following retraction of needle 34 and removal of tip 26 from tubular section 84 of hub 80.

Referring to FIG. 2, IV catheter introducer 10 of the invention is preferably assembled by dropping retraction spring 16 through opening 22 into housing 12. Retraction spring 16, which is a coil spring biased against compression, preferably has a diameter that causes it to seat just above inclined annular shoulder 94 inside housing 12, where it is supported in substantially vertical alignment by section 33 of sidewall 28. Pre-manufactured needle holder assembly 14 is then inserted downwardly through open end 22 of housing 12, with beveled end 48 of needle 34 passing downwardly through retraction spring 16 and tip 26 of housing 12, until inclined annular shoulder 96 of tubular body 32 abuts against shoulder 94 of housing 12. Alternatively, spring 16 can be placed over needle holder assembly 14 prior to insertion of needle holder assembly 14 into housing 12.

Also, if desired, needle 34 can be glued or sonically welded into needle holder assembly 14 after needle holder assembly 14 is inserted into housing 12. Inclined annular shoulder 92 of tubular body 32 preferably will not contact inclined annular shoulder 98, to permit shoulder 96 to seat properly against shoulder 94.

Referring to FIGS. 2 and 4, lower end portion 56 of pre-manufactured plunger assembly 18 is next introduced into housing 12 through opening 22. As plunger tube 40 travels downwardly into housing 12, nose 104 of plunger tube 40 reaches and slides over end 52 of tubular body 32 of needle holder assembly 14. When nose 104 reaches end 52, radially extending annular boss 100 on plunger tube 40 is still disposed above inwardly projecting annular ring 102 of housing 12, and the inside diameter of plunger tube 40 at nose 104 is sufficiently greater than the outside diameter of end 52 to permit lower end portion 56 of plunger tube 40 to slidably engage the portion of tubular body 32 that is adjacent to end 52. As plunger assembly 18 is inserted farther into housing 12, annular boss 100 engages and overrides annular ring 102. Annular ring 102 then resists rearward movement of plunger tube assembly 18 and combined needle holder assembly 14 once they are installed in the housing with the needle extended for use. If there is an attempt to withdraw the plunger tube assembly 18 from housing 12, the shoulder of annular boss 100 will contact the shoulder of annular ring 102 and prevent the withdrawal unless there is an exertion of substantial force. However, it should be understood that annular ring 102 is desirably sufficiently small to allow for the withdrawal of a molding tool during the manufacturing process. Referring to FIG. 4, a detail view taken from FIG. 2, plunger tube 40 continues to slide downwardly over tubular body 32 of the needle holder assembly until inwardly facing annular boss 106 on the inside surface of lower end portion 56 reaches and snaps into engagement with cooperatively sized and aligned, outwardly facing annular recess 108 of tubular body 32. Referring to FIGS. 2 and 4, the configuration and dimensions of annular boss 106 and annular recess 108 cause boss 106 to be biased radially inward into annular recess 108.

It should be understood that boss 106 on the inside of plunger tube 40, is not required to be circumferentially coextensive with annular recess 108 of tubular body 32. Thus, for example, boss 106 can instead comprise a circumferentially spaced array of discrete, inwardly extending bumps that are biased into engagement with recess 108. It is preferred, however, that recess 108 extend completely around tubular body so that the slidable engagement between plunger tube 40 and tubular body 32 does not require a specific rotational alignment between the two parts. The configuration and dimensions of boss 106 and recess 108 are preferably such that the force required to slidably disengage boss 106 from recess 108 by forcing plunger tube 40 farther down into housing 12 is greater than the biasing force being exerted against needle holder assembly 14 by compressed retraction spring 16 and by the additional force that is exerted upwardly on the needle 34 during catheter insertion procedures. IV catheter 20 can be assembled to tip 26 of housing 12 prior to the insertion of needle holder assembly 14 and plunger assembly 18 into housing 12. Alternatively, plunger assembly 18 and needle holder assembly 14 (sometimes referred to as a needle support assembly) can also be assembled to each other prior to insertion into housing 12. The frictional engagement between boss 106 and recess 108 when they are cooperatively engaged is preferably sufficient to permit needle holder assembly 14 and plunger assembly 18 to be inserted together into housing 12.

Beveled needle end 48 and a portion of cannula 78 are desirably inserted into a patient's vein while grasping annular ridges 31 of housing 12 with the thumb and fingers. Following insertion of the catheter into a patient, needle holder assembly 14 is retracted by grasping wings 30 or annular ridges 31 with one's fingers, or thumb and fingers, and then using the palm or heel of the hand against end cap 66 to force plunger tube 40 farther down into housing 12. When this occurs, the frictional engagement between boss 106 and recess 108, as seen in FIG. 4, is over-pressured, causing boss 106 to ride up onto surface 112 of tubular body 32. Continued downward movement of plunger tube 40 relative to tubular body 32, which is firmly seated against housing 12, causes boss 106 to drop off inclined shoulder 114 of tubular body 32. When this occurs, there is no remaining significant frictional force being exerted against compressed retraction spring 16, and spring 16 rapidly expands, causing needle holder assembly 14 to be propelled upwardly into retraction cavity 76, simultaneously withdrawing needle 34 at least to a position where beveled end 48 is withdrawn into housing 12.

Referring to FIG. 3, retraction spring 16 is fully expanded and top end 52 of needle holder assembly 14 is at least partially withdrawn into retraction cavity 76. Air previously present in retraction cavity 76 of plunger tube 40 has been vented through vent hole 72 as needle holder assembly 14 moved upwardly within the cavity in response to expansion by retraction spring 16. Top end 52 of needle holder assembly 14 has moved upward within retraction cavity 76 sufficiently that beveled end 48 of needle 34 is withdrawn into housing 12. When needle 34 is in the position shown in FIG. 3, tip 26 of housing 12 can be safely detached from IV hub 80.

The improved IV catheter introducer of the invention is well suited for automated manufacture and assembly. Aside from the catheter, needle and spring, only a housing, retractable needle holder and a capped, vented plunger tube are needed. Although housing 12 can be made in a straight configuration with a straight internal wall, it is preferably made with a stepped configuration that, with the exception of the lower shoulder of annular ring 102, tapers inwardly from top to bottom. This taper makes it easy to withdraw a core mandrel used in the molding process. Although not illustrated in the drawings, it should be understood that beveled end 48 of needle 34 is preferably protected during the manufacturing process, shipping and storage by a tubular cover that slides upwardly over the outside of cannula 78, preventing the needle from being damaged.

An important aspect of the subject IV catheter introducer is the fact that the operator can conveniently operate the retractable introducer structure with one hand. One handed operation is possible because the plunger tube desirably extends about 1.5 to about 3 inches past where the wings of the housing are located. This allows force to be applied against the plunger tube by the fleshy part of the palm while using the fingers behind the wings or the annular ridges of the housing to resist the force and smoothly initiate retraction. The other hand remains free to grasp the hub of the catheter. Timing for freeing the hub from the introducer device and attaching an IV tube to the hub is under complete control of the operator. In one motion, the hub of the catheter can be separated from the insertion device, which can then be safely set aside while the connection is then made to the IV tube or other device that is to be connected to the patient. The catheter introducer can be safely set aside without concern onto a bed or tray, because the needle has already been safely retracted before the catheter assembly is disconnected from the housing. When the fingers pull back on the wings or annular ridges of the housing to trigger retraction, the operator can both hear and see that the needle is safely retracted and immediately disengage and safely set aside the device to free his hand for use in making the necessary IV connection before loss of fluid from the patient occurs.

The IV catheter introducer of the invention does not have to resist as much force imposed by the needle on the retraction parts as does a conventional syringe that is required to puncture a rubber seal commonly used on vials. Consequently, the retractable parts need only be able to resist the force encountered during normal clinical use without retracting. With the apparatus disclosed herein, dimensional tolerances and differential thermal expansion rates are less critical than with devices where the only frictional engagement is provided by surface-to-surface contact between smooth facing surfaces.

The IV catheter introducer disclosed herein is less likely to retract the needle prematurely than prior art devices, even when subjected to rough handling and widely varying temperatures and humidity during shipment and storage prior to use. The invention has a simple, streamlined shape and a retraction spring that is simpler to operate and more reliable than others previously used. The device can be operated with one hand in any rotational position where the wings are accessible because it has no external latches that require placing the device in a particular orientation. Further, the wings prevent the catheter introducer from rolling when placed on an oblique surface. With the device held in the hand, the retraction force is applied linearly along the main longitudinal axis. A very short stroke movement is sufficient to trigger retraction. Successful retraction is noted both visually and audibly because the operator can easily see the retracted parts in the housing and retraction creates an unobtrusive noise.

Other alterations and modifications of the preferred embodiment described above will become apparent to those of ordinary skill in the art upon reading this disclosure, and it is intended that the scope of the invention disclosed herein be limited only by the broadest interpretation of the appended claims to which the inventor is legally entitled.

What is claimed is:

1. An IV catheter introducer comprising a tubular housing; a needle holder assembly which has a tubular body in shape is slidably engaged inside the housing; a retraction mechanism seated in an annular space between the housing and the needle holder assembly; a plunger assembly having a plunger tube releasably engaged with the tubular body inside the housing; and a catheter attached by frictional engagement to the tubular housing; wherein the tubular body comprises an outwardly facing annular recess proximal to the plunger tube;

the plunger tube comprises an outwardly extending annular boss proximal to the tubular body; and the annular recess and annular boss are biased into releasable engagement with each other.

2. The IV catheter introducer of claim 1 wherein the retraction mechanism is a spring.

3. The IV catheter introducer of claim 2 wherein the spring is a compressed spring.

4. The IV catheter introducer of claim 1 wherein the tubular housing and tubular body are made of clear plastic.

5. The IV catheter introducer of claim 4 wherein the clear plastic comprises polycarbonate.

6. The IV catheter introducer of claim 4 wherein the needle holder assembly comprises a flash chamber with an interior space that is viewable through no more than two layers of clear plastic.

7. The IV catheter introducer of claim 6 wherein the needle holder assembly has a needle with an end that extends into the flash chamber.

8. The IV catheter introducer of claim 1 wherein the plunger tube has a vented end that is distal to the tubular body.

9. The IV catheter introducer of claim 8 wherein the vented end comprises a plastic end cap.

10. The IV catheter introducer of claim 9 wherein the plastic end cap is colored.

11. The IV catheter introducer of claim 8 wherein the vented end comprises an end cap having a vent hole and irregular surface features surrounding the vent hole.

12. The IV catheter introducer of claim 8 wherein the vented end comprises an end cap having an annular skirt that frictionally engages the plunger tube.

13. The IV catheter introducer of claim 8 wherein the vented end comprises a glued end cap.

14. The IV catheter introducer of claim 8 wherein the vented end comprises a sonically welded end cap.

15. The IV catheter introducer of claim 8 wherein the vented end comprises an end cap that is dual shot molded onto the plunger tube.

16. The IV catheter introducer of claim 1 wherein the needle holder assembly has an insert molded needle.

17. The IV catheter introducer of claim 1 wherein a needle is glued into needle holder assembly.

18. The IV catheter introducer of claim 1 wherein a needle is sonically welded into needle holder assembly.

19. The IV catheter introducer of claim 1 wherein the tubular body has a plugged end comprising an inwardly facing annular recess in the tubular body and a porous plug inserted into frictional engagement with the annular recess.

20. The IV catheter introducer of claim 19 wherein the annular recess in the tubular body is adjacent to an outwardly tapered interior wall section of the tubular body.

21. The IV catheter introducer of claim 1 wherein the tubular body further comprises a reduced diameter section that is longitudinally spaced apart from the annular recess, and wherein the plunger tube is disengageable from the tubular body by an application of force to the plunger tube that is sufficient to slide the annular boss out of the annular recess and along the tubular body to a point opposite the reduced diameter section.

22. The IV catheter introducer of claim 21 wherein the needle holder assembly is forced into the plunger tube by the retraction mechanism when the annular boss is opposite the reduced diameter section.

23. The IV catheter introducer of claim 1 wherein the tubular housing comprises an open end and a plurality of laterally extending wings adjacent to the open end.

24. The IV catheter introducer of claim 1 wherein the catheter further comprises a cannula depending from a hub attachable to the tubular housing.

25. An IV catheter introducer comprising a tubular housing; a needle holder assembly which has a tubular body in shape is slidably engaged inside the housing; a retraction mechanism seated in an annular space between the housing and the needle holder assembly; a plunger assembly having a plunger tube releasably engaged with the tubular body inside the housing; and a catheter attached by frictional engagement to the tubular housing; wherein the plunger tube comprises a vented end that is opposite the tubular body.

26. The IV catheter introducer of claim 25 wherein the vented end comprises a plastic end cap.

27. The IV catheter introducer of claim 26 wherein the plastic end cap is colored.

28. The IV catheter introducer of claim 25 wherein the vented end comprises an end cap having a vent hole and irregular surface features surrounding the vent hole.

29. The IV catheter introducer of claim 25 wherein the vented end comprises an end cap having an annular skirt that frictionally engages the plunger tube.

30. The IV catheter introducer of claim 25 wherein the vented end comprises a glued end cap.

31. The IV catheter introducer of claim 25 wherein the vented end comprises a sonically welded end cap.

32. The IV catheter introducer of claim 25 wherein the vented end comprises an end cap that is dual shot molded onto the plunger tube.

33. The IV catheter introducer of claim 25 wherein the retraction mechanism is a spring.

34. The IV catheter introducer of claim 33 wherein the spring is a compressed spring.

35. The IV catheter introducer of claim 25 wherein the tubular housing and tubular body are made of clear plastic.

36. The IV catheter introducer of claim 35 wherein the clear plastic comprises polycarbonate.

37. The IV catheter introducer of claim 35 wherein the needle holder assembly comprises a flash chamber with an interior space that is viewable through no more than two layers of clear plastic.

38. The IV catheter introducer of claim 37 wherein the needle holder assembly has a needle with an end that extends into the flash chamber.

39. The IV catheter introducer of claim 25 wherein the needle holder assembly has an insert molded needle.

40. The IV catheter introducer of claim 25 wherein a needle is glued into needle holder assembly.

41. The IV catheter introducer of claim 25 wherein a needle is sonically welded into needle holder assembly.

42. The IV catheter introducer of claim 25 wherein the tubular body has a plugged end comprising an inwardly facing annular recess in the tubular body and a porous plug inserted into frictional engagement with the annular recess.

43. The IV catheter introducer of claim 42 wherein the annular recess in the tubular body is adjacent to an outwardly tapered interior wall section of the tubular body.

44. The IV catheter introducer of claim 25 wherein the tubular housing comprises an open end and a plurality of laterally extending wings adjacent to the open end.

45. The IV catheter introducer of claim 25 wherein the catheter further comprises a cannula depending from a hub attachable to the tubular housing.

46. An IV catheter introducer comprising a needle holder assembly and a plunger assembly coaxially aligned and slidably engaged inside a tubular housing, a catheter releasably attached to the tubular housing, and a retraction mechanism biasing the needle holder assembly toward the plunger assembly, wherein:
  the needle holder assembly comprises an elongated tubular body having a first end supporting a hollow needle with a beveled end, a second end containing a frictionally engaged porous plug, a flash chamber disposed between the first and second ends and in fluid communication with the hollow needle, and an outside wall having an annular recess disposed near the second end;
  the plunger assembly comprises an elongated plunger tube having an open end that is slidably engaged over the second end of the tubular body of the needle holder assembly, a vented end opposite the open end, and engagement structure projecting radially inward near the open end;
  the engagement structure being biased into engagement with the annular recess of the needle holder assembly with a force sufficient to prevent the needle holder assembly from being moved toward the plunger assembly by the retraction mechanism.

47. The IV catheter introducer of claim 46 wherein the tubular body further comprises a relief structure into which the engagement structure can be moved by manually overpressuring the biasing force of the engagement structure to disengage the engagement structure from the annular recess.

48. The IV catheter introducer of claim 46 wherein the engagement structure is an annular boss.

49. The IV catheter introducer of claim 46 wherein the plunger tube comprises a retraction cavity sufficiently large to receive at least a portion of the needle holder assembly therein during retraction of the needle to a position where the beveled end is inside the tubular housing.

50. The IV catheter introducer of claim 46 wherein the vented end of the plunger tube comprises a frictionally engaged vent cap.

51. The IV catheter introducer of claim 50 wherein the vent cap comprises a vent hole and surface relief structures surrounding the vent hole.

52. The IV catheter introducer of claim 46 wherein the vented end comprises a glued end cap.

53. The IV catheter introducer of claim 46 wherein the vented end comprises a sonically welded end cap.

54. The IV catheter introducer of claim 46 wherein the vented end comprises an end cap that is dual shot molded onto the plunger tube.

55. The IV catheter introducer of claim 46 wherein the tubular housing and the tubular body are made of clear plastic.

56. The IV catheter introducer of claim 46 wherein the retraction mechanism is a spring.

57. The IV catheter introducer of claim 56 wherein the spring is a compressed spring.

58. The IV catheter introducer of claim 46 wherein the catheter further comprises a cannula through which the hollow needle extends.

59. An IV catheter introducer comprising a tubular housing; a needle holder assembly which has a tubular body in shape is slidably engaged inside the housing; a retraction mechanism seated in an annular space between the housing and the needle holder assembly; a plunger assembly having a plunger tube releasably engaged with the tubular body inside the housing; and a catheter attached by frictional engagement to the tubular housing; wherein
  the tubular housing comprises an open end and a plurality of laterally extending wings adjacent to the open end.

60. The IV catheter introducer of claim 59 wherein the tubular housing comprises an open end and a plurality of laterally extending wings adjacent to the open end.

61. An IV catheter introducer comprising:
  a clear plastic tubular housing having a wide end, a narrow end, a stepped inside diameter between the wide and narrow ends, and laterally extending wings adjacent the wide end;
  a needle holder assembly seated inside the housing, comprising a hollow needle with a beveled end, a needle support member holding the needle in coaxial alignment with the housing, a clear plastic flash chamber in fluid communication with the hollow needle, a porous plug sealing an end of the flash chamber opposite the hollow needle, and an annular recess facing radially outward near the sealed end of the flash chamber;

a plunger assembly further comprising a clear plastic plunger tube with an open end insertable into the housing around a portion of the needle holder assembly, a retraction cavity sufficiently large to accommodate withdrawal of the beveled end of the needle into the housing upon retraction, a first structure projecting radially outward to engage the housing, and a second structure projecting radially inward to engage the annular recess; and a vented end cap sealing the plunger tube opposite the open end;

a retraction mechanism compressed inside the housing around the needle support assembly and biasing the needle support assembly toward the retraction cavity of the plunger tube; and a catheter frictionally engaging the narrow end of the housing and further comprising a cannula coaxially aligned with and slidably disposed over the hollow needle; wherein the second structure engages the annular recess to prevent the needle support assembly from moving into the retraction cavity under the bias of the retraction mechanism and any additional force exerted upwardly on the needle during insertion of the cannula into a patient.

62. A method for assembling an IV catheter introducer comprising the steps of:

providing a tubular housing with a wide end, a narrow end and a stepped inside wall;

providing a needle support assembly comprising a tubular body holding a hollow needle in coaxial alignment with and in fluid communication with a substantially cylindrical flash chamber, the flash chamber being plugged at an end opposite the needle with a porous plug, the tubular body also having a spring guide section and an outwardly facing annular recess near the plugged end;

providing a coiled retraction spring slidably engageable with the spring guide section of the tubular body;

providing a plunger assembly comprising a plunger tube having an open end and a vented end, the plunger tube having an outwardly projecting structure and an inwardly projecting structure near the open end;

providing a catheter comprising a cannula and a tubular hub;

attaching the tubular IV hub to the narrow end of the housing;

inserting the coiled retraction spring into the wide end of the housing in coaxial alignment with the housing;

inserting the needle support assembly into the wide end of the housing in coaxial alignment with the housing, causing the needle to slide downwardly through the retraction spring and the cannula until the tubular body is seated inside the housing and the retraction spring is disposed around the spring guide;

inserting the plunger tube into the wide end of the housing in coaxial alignment with the housing and with the needle support assembly, and causing the open end of the plunger tube to override the plugged end of the needle holder assembly until the outwardly projecting structure engages the stepped inside wall of the housing and the inwardly projecting structure engages the annular recess, thereby compressing the retraction spring and maintaining the retraction spring in its compressed state by the engagement between the inwardly projecting structure and the annular recess.

63. The method of claim 62 wherein the retraction spring is placed over the needle support assembly before the needle support assembly is inserted into the wide end of the housing.

64. The method of claim 62 wherein the plunger tube is engaged with the needle support assembly before the needle support assembly is inserted into the wide end of the housing.

65. The method of claim 62 wherein the needle support assembly is first provided without a needle, and the needle is later glued into the needle support assembly following insertion of the needle support assembly into the housing.

66. The method of claim 62 wherein the needle support assembly is first provided without a needle, and the needle is later sonically welded into the needle support assembly following insertion of the needle support assembly into the housing.

* * * * *

UNITED STATES PATENT AND TRADEMARK OFFICE
CERTIFICATE OF CORRECTION

PATENT NO. : 6,872,193 B2
DATED : March 29, 2005
INVENTOR(S) : Thomas J. Shaw et al.

It is certified that error appears in the above-identified patent and that said Letters Patent is hereby corrected as shown below:

Column 10,
Lines 49 and 50, delete in their entirety and insert:
-- the tubular body of the needle holder comprises an upper end portion and a needle support section, the upper end portion comprising an outwardly facing annular recess releasably engaged with an outwardly extending annular boss on the plunger tube, the needle support section extending through the retraction mechanism and protruding forwardly beyond the tubular housing. --

Signed and Sealed this

Twelfth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,872,193 B2  Page 1 of 1
APPLICATION NO. : 10/047662
DATED : March 29, 2005
INVENTOR(S) : Thomas J. Shaw et al.

It is certified that error appears in the above-identified patent and that said Letters Patent is hereby corrected as shown below:

<u>Column 10,</u>
Lines 49 and 50, delete in their entirety and insert:
-- the tubular body of the needle holder comprises an upper end portion and a needle support section, the upper end portion comprising an outwardly facing annular recess releasably engaged with an inwardly extending annular boss on the plunger tube, the needle support section extending through the retraction mechanism and protruding forwardly beyond the tubular housing. --

This certificate supersedes the Certificate of Correction issued July 12, 2005.

Signed and Sealed this

Eighteenth Day of March, 2008

JON W. DUDAS
*Director of the United States Patent and Trademark Office*